US006846626B1

(12) United States Patent
Senapathy

(10) Patent No.: US 6,846,626 B1
(45) Date of Patent: Jan. 25, 2005

(54) METHOD FOR AMPLIFYING SEQUENCES FROM UNKNOWN DNA

(75) Inventor: Periannan Senapathy, Madison, WI (US)

(73) Assignee: Genome Technologies, LLC, Madison, WI (US)

( * ) Notice: Subject to any disclaimer, the term of this patent is extended or adjusted under 35 U.S.C. 154(b) by 0 days.

(21) Appl. No.: 09/431,451

(22) Filed: Nov. 1, 1999

Related U.S. Application Data

(60) Provisional application No. 60/151,975, filed on Sep. 1, 1999.

(51) Int. Cl.[7] .......................... C12Q 1/68; C12P 19/34; C07H 21/02; C07H 21/04
(52) U.S. Cl. ....................... 435/6; 435/91.2; 536/23.1; 536/24.3; 536/24.33; 536/25.3
(58) Field of Search .................. 435/6, 91.1, 91.2, 435/183; 436/94; 536/23.1, 24.3, 24.33, 25.3

(56) References Cited

U.S. PATENT DOCUMENTS

| | | | | |
|---|---|---|---|---|
| 5,200,313 | A | * | 4/1993 | Carrico .......................... 435/6 |
| 5,508,169 | A | * | 4/1996 | Deugau et al. ................. 435/6 |
| 5,807,679 | A | * | 9/1998 | Kamb ............................ 435/6 |
| 6,521,428 | B1 | * | 2/2003 | Senapathy ................. 435/91.2 |
| 6,528,288 | B2 | * | 3/2003 | Senapathy ................. 435/91.2 |

OTHER PUBLICATIONS

Sommer and Tautz, "Minimal homology requirements for PCR," Nucleic Acids Research, vol. 17, No. 16 (1989), p. 6749.*
Bowie, et al., *Science*, 247:1306 (1990)).
Deeb, S.S., et al., *Am. J. Hum. Genet.*, 46:822 (1990).
Duyk, G.M., et al., *Proc. Natl. Acad. Sci. USA*, 87:8995–9 (1990).
Estivill, X. and Williamson, R., *Nucleic Acids Res.*, 15:1415–25 (1987).
Fuentes, J.J., et al., *Hum. Genet.* 101:346–50 (1997.
Jendraschak, E. and Kaminski, W.E., *Genomics*, 50:53–60 (1998).
Lim, J., et al., *Mol. Cell. Endocrinol.*, 131:205 (1997).
Lovett, M., et al., *Proc. Natl. Acad. Sci. USA*, 88:9628–32 (1991).
Myerowitz, T., *Proc. Natl. Acad. Sci. USA*, 85:3955 (1988).
O Neill, M.J., et al., *Hum. Mutat.*, 11:340 (1998).
Reissner, K., et al., *Mol. Genet. Metab.*, 63:281 (1998).
Rommens, et al., *Science*, 245:1059–80 (1989).
Senapathy, P., *Proc. Natl. Acad. Sci.*, 83:2133–2137 (1986).
Senapathy, P. et al., RNA splice junctions of different classes of eukaryotes: Sequence statistics and functional implications in gene expression, Nucleic Acids Research, vol. 15, No. 17, pp. 7155–7176 (1987).
Senapathy, P., *Proc. Natl. Acad. Sci.*, 85:1129–1133 (1988).
Senapathy, P., *Molecular Genetics (Life Sci. Adv.)*, 7:53–65 (1988).
Senapathy, P., et al., 1990. Splice junctions, branch point sites, and exons: Sequence statistics, identification, and applications to the Genome Project, in *Methods in Enzymology, Computer Analysis of Protein and Nucleic Acid Sequences*, Doolittle, R.F., ed., 183:252–278.
Tajima, T., et al., *Endoc. J.*, 45:291 (1998).
Wilson, R., et al., *Nature*, 368:32–38 (1994).

* cited by examiner

*Primary Examiner*—Bradley L. Sisson
(74) *Attorney, Agent, or Firm*—Joseph T. Leone, Esq.; DeWitt Ross & Stevens S.C.

(57) ABSTRACT

Disclosed is a method of specifically amplifying desired regions of nucleic acid from a sample containing nucleic acid. The method includes providing a plurality of first PCR primers, each first primer having a region of fixed nucleotide sequence identical or complementary to a consensus sequence of interest and a region of randomized nucleotide sequence located 5' to, 3' to, anywhere within, or flanking the region of fixed nucleotide sequence; providing a plurality of second PCR primers, each second primer having a region of arbitrary, yet fixed nucleotide sequence and a region of randomized nucleotide sequence located 5' to, 3' to, anywhere within, or flanking the region of fixed nucleotide sequence; and then amplifying the nucleic acid present in the sample via the PCR using the plurality of first PCR primers and the plurality of second PCR primers; whereby a subset of the plurality first primers binds to the consensus sequence of interest substantially wherever it occurs in the sample, and a subset of the plurality of second primers binds to the sample at locations removed from the first primers such that DNA regions flanked by the first primer and the second primer are specifically amplified.

26 Claims, 9 Drawing Sheets

| | |
|---|---|
| 5' splice junction: | AGGT⁽ᴬ/G⁾GGT |
| 3' splice junction: | (TT/CC)(TT)(TTTTTT/CCCCCC)XAGGT |
| Promoter region: | TATAA |
| Poly A: | ATAATA |
| Alu repeats: | Repeats of about 250 bases |
| Homeobox: | A sequence of about 180 bases coding for ~ 60 amino acids |

5' Splice Consensus Primer

Promoter Consensus Sequence:

METHOD FOR AMPLIFYING SEQUENCES FROM UNKNOWN DNA

Priority is hereby claimed to provisional application Ser. No. 60/151,975, filed Sep. 1, 1999, and incorporated herein by reference.

BACKGROUND OF THE INVENTION

The human genome harbors the genetic variations for a large number of Mendelian disorders. Many of these disorders have been localized in the genome through linkage studies, and the genes for these disorders are being isolated by different methods. The techniques currently used for isolating genes include: cDNA selection (Lovett, M., et al., Proc. Natl. Acad. Sci. USA, 88:9628–32 (1991)), exon trapping (Duyk, G. M., et al., Proc. Nail. Acad. Sci. USA, 87:8995–9 (1990)), CpG island identification (Estivill, X. and Williamson, R., Nucleic Acids Res., 15: 1415–25 (1987)), hybridization using genomic fragments as probes against cDNA libraries (Rommerns, et al., Science, 245:1059–80 (1989)), cloning and sequencing of genomic DNA followed by computer analysis of the possible coding regions (Wilson, R., et al., Nature, 368:32–38 (1994)), Alu-splice PCR (Fuentes, J. J., et al., Hum. Genet. 101:346–50 (1997)), and Alu-promoter PCR (Jendraschak, E. and Kaminski, W. E., Genomics, 50:53–60 (1998)).

These techniques have several limitations. For example, many require analyzing large numbers of subclones to yield meaningful results. Both cDNA selection and hybridization using genomic fragments depend upon gene expression patterns using cDNA or mRNA libraries. Exon trapping requires specialized vectors and cell culture materials; whilst cDNA selection results only in an enrichment of expressed sequences from a specific RNA source followed by much time and effort to determine the origin of the selected cDNAs. Alu-splice PCR also has limitations in that it can identify only a few putative exons out of a larger number of true exons, even in a YAC clone. Because none of these methods permit the isolation of all the genes in a given region, normally several of the above methods are used in conjunction to complement one another, thereby achieving more complete results.

Furthermore, these methods are most usually only applied to DNA regions included in vectors such as yeast artificial chromosomes (YACs), bacterial artificial chromosomes (BACs), plasmids, and cosmids. They cannot be applied directly to whole genomic DNA for isolating a majority of the exons of genes contained in the genome. A method for isolating the majority of the flanking regions to a signal sequence, such as the 3' or the 5' splice junction or the promoters, present at numerous locations in a genome with a consensus sequence, would be very a advantageous in a variety of genetic studies for discovering and treating major illnesses.

In essence, current methods for specifically amplifying exons present in an fir; unknown genomic DNA are limited in their abilities. The isolation of only exon sequences from a gene will be advantageous for a variety of applications including comparative analysis between individuals. Attempts have been made to use the above methods to accomplish this purpose using genomic DNA fragments cloned into vectors.

For example, the Alu-splice PCR method attempts to isolate exon-containing fragments from cloned genomic DNA. This method utilizes the consensus sequence of splice junctions linked to a restriction enzyme recognition sequence as one primer and the consensus sequence of Alu repeat elements as the other primer to amplify any potential exon sequence that may be present between these primer binding sites in a cloned YAC DNA. The results of this method are poor for many reasons. For example, in one study, from a total of 128 colonies picked, only ten contained putative exons. Furthermore, out of the few genes present in the two YACs analyzed, none of the nine exons present in one of the genes was isolated. Further still, most of the exons from among the five new genes that possibly existed in these YACs were not isolated except for one or two exons. From among the ten putative exon sequences isolated, six were shorter than 350 nucleotides. As the authors of this study agree, not all genes in a given sample will be identified by Alu-splice PCR, and not all the exons within a given gene will be identified by Alu-splice PCR. There are at least two reasons that explain this outcome: 1) the paucity of conveniently placed Alu repetitive elements; and 2) the limiting factor of specificity of the 5' and 3' splice-site primers; in the best of cases, primer specificity is only eight nucleotides. These inadequate results, even with a relatively short template DNA (YAC) compared to genomic DNA, indicate that this method is not applicable to isolate, in multiplex fashion, the exons of many genes from whole genomic DNA.

SUMMARY OF THE INVENTION

In contrast, the present invention is able to amplify specifically a majority of the exons from most genes from a whole genomic DNA sample. The present invention can also be used on samples such as sub-genomic DNA, cloned genomic DNA, individual chromosomes, and sub-chromosomal DNA. The invention overcomes the deficiencies of the prior art methods because it functions on genomic DNA, rather than requiring extensive cloning and sub-cloning of sample DNA.

Signal sequences identifying the location of genes of interest are usually much shorter than the standard primer length normally used in PCR reactions. For example, the promoter consensus sequence (5 nucleotides), poly A site (6 nucleotides), 5' splice junction (8 nucleotides), and the 3' splice junction (10 nucleotides) are shorter than the 16–25 nucleotides used in standard PCR primers.

In the invention, the length of a consensus primer is increased by adding randomized nucleotides (Ns) to the consensus sequence of any gene-control signal, such as a promoter or a splice junction, thereby increasing the length of the primer to a standard primer length. The additional randomized nucleotides increase the length, the specificity, and the total affinity of binding of a primer to its respective binding site by providing all possible sequences in the randomized portion of the primer. In contrast, when using the Alu-splice primer, the best possible scenario (e.g., with the 5' splice site) had an 8 nucleotides specificity (Fuentes, J. J., et al., Hum. Genet., 101:346–50 (1997)), and the remainder of the primer consisted of a restriction recognition site.

The current invention, however, uses a number of randomized nucleotides linked to the splice junction consensus sequence, with each of the primer species in the primer preparation having a full complementarity with a particular splice junction present at a unique location in the whole genome. Approximately 500,000 to 1,000,000 exons are expected to be present in the whole human genome for a total estimated 100,000 genes. A sequence with ten randomized nucleotides will have $4^{10}$ (i.e., 1,048,576), different possible sequences. Thus, a 3' splice junction consensus sequence linked to ten additional bases of randomized sequence (i.e., $N_{10}$ where N is A, C, T, or G) will bind to approximately one million different but uniquely specific splice junctions in the human genome. By increasing the concentration of each of the primer species in the primer preparation many thousand fold, it has been found that standard PCR amplification proceeds normally. For example, using a 5000-fold increase in primer concentration in a standard PCR reaction, genomic DNA can be amplified specifically so that only the exons present within the genomic DNA are amplified.

In the current method, a primer of partly-fixed sequence is used as the second primer. This primer, and the method of utilizing a primer of partially fixed sequence, is the subject matter of approved patent application Ser. No. 08/406,545 to the subject inventor, the entirety of which is incorporated herein. The partially-fixed primer is comprised of a fixed base sequence of defined length, and a randomized sequence component. By virtue of binding at a defined mean length from the first primer, a mean length which is determined by the number of fixed nucleotides, it enables the amplification of a defined average length of a DNA fragment from the first primer binding site. Thus, using a partly-fixed consensus primer as the first primer and a partly-fixed second primer, theoretically all the sequences downstream of the locations where the consensus primers bind can be amplified specifically from a given genomic DNA. Even if in practice all of the possible target sequences are not amplified due to extreme $T_M$ ranges that may be required for their amplification, a considerable number of such sequences will be amplified, which is very advantageous and a great improvement over the prior art methods.

An important concept of the present invention is that by adding randomized nucleotides to any consensus sequence of less-than-optimum primer length, the primer cocktail will then contain a large plurality of full-length primers, each of which primer includes the consensus sequence within it (see FIG. 1). Each individual primer species within the primer cocktail is a full-length primer, with the capability of binding with standard complementarity at a specific location within a genomic DNA sample which exhibits the consensus sequence. Because genomic DNA has essentially random sequence characteristics, it lends itself to such random sequence manipulation (Senapathy, P., Proc. Natl. Acad. Sci., 83:2133 (1986); ibid, 85:1129 (1988); ibid, Molecular Genetics (Life Sci. Adv.), 7:53 (1988); Senapathy, P., et al., Methods in Enzymology, 183:252 (1990)).

Depending upon the number of randomized nucleotides added to the fixed consensus sequence, an increased concentration of any given primer or sub-set of primers can be used to increase the mole equivalent of a particular primer species to that of the primer concentration normally used in standard PCR reaction. Thus, the current method is uniquely suited for the application of PCR to amplify multiple genomic DNA regions comprising consensus sequences of sub-optimal primer length. The invention thereby amplifies fragments from multiple locations within genomic DNA which flank the consensus sequence(s) or which include the consensus sequence(s).

The same method can be applied to shorter genomic template DNA fragments, such as a specific chromosomal DNA, or even YAC, BAC, or plasmid DNA. In all instances, the correct subspecies from the primer cocktail will bind to its complementary sequence in DNA fragments which are shorter than genomic DNA, while the rest of the primer species will not bind anywhere else in the target DNA under standard PCR conditions.

The invention is applicable for isolating not only exons and their flanking regions from a genomic DNA, but also regions flanking other consensus sequences, such as promoter sequences and poly A sequences. Single nucleotide polymorphisms (SNPs) are expected to be present in and around these regulatory regions across individuals of the human population. These single base substitutions are expected to facilitate association studies to identify genes involved in particular phenotypes or genetic diseases.

Isolating different promoter sequences and their flanking regions present in a genome also enables the creation of identifiable addresses with a unique primer pair for each unique promoter within a unique gene, so that the same promoter and flanking region can be analyzed across many individuals. This identification is enabled by the present invention by creating a primer that includes the promoter signal consensus sequence and an appropriate number of randomized nucleotides to make the primer a full-length primer. Each of the different sub-species of primers from the primer preparation will bind to a different, unique promoter, thereby amplifying the specific region downstream of the promoter. The advantage here is that, although the promoter is only a 5 nucleotide consensus sequence, a full-length primer is provided with complementarity over the length of the entire primer to the unique sequence surrounding the promoter at each site of binding. This process enables the isolation of most of the specific promoter sequences out of all the 100,000 or so genes estimated to be present in a mammalian genome.

It is standard practice to add a different restriction enzyme recognition site (usually so called "rare-cutter" sites) at the end of each of the primers between which targeted sequences are amplified. The presence of the recognition sites allows for digestion or partial digestion of the amplified fragment using restriction enzymes which recognize the added sites, and then linking the digested fragments to a vector having complementary sticky ends. In this fashion, only the target sequences (as opposed to any nonspecifically amplified sequences) are cloned and propagated. Alternatively, if most clones are expected to contain specific sequences, blunt end cloning can be used. Such a method is also adapted in the current invention for the purpose of cloning specific fragments.

Mutations causing many genetic disorders are generally thought to be localized within genes rather than within intergenic regions. A survey of the literature, combined with further analysis indicates that, within genes, single nucleotide polymorphisms (SNPs) and other functional sequence variations can be expected to be present within exons and their immediate flanking regions within introns, rather than in regions well interior in introns. Likewise, mutations are also likely to be found within promoter sites and poly A sites and their flanking regions. There is also the possibility that many more SNPs may be present in these transcriptional and translational control regions, or regulatory regions such as promoters, splice junctions, and poly A sites, than in protein coding regions. By way of illustration, many cancers and heritable disorders such as thalasemias are known to be caused by such mutations. Moreover, the probability of a mutation in these regions leading to a drastically changed protein product is higher than mutations in coding regions, since most (95%) of the mutations in the coding regions lead to silent amino acid substitutions which do not alter the structure or the function of the protein (Bowie, et al., Science, 247:1306 (1990)).

In contrast, any mutation in a regulatory sequence, sequences which are very short in comparison to coding regions, will have a higher probability of causing drastic variation in the expression of the protein, thereby resulting in a drastically altered protein structure, synthesis, or secretion, thereby leading to a drastic phenotypic variation. It is well known that mutations within or around splice junction sequences can cause truncated proteins or proteins wherein an exon is missing, or amino acid residues from a spurious open reading frame have been added to the previous exon.

For example, a single nucleotide mutation at the 5' splice junction sequence causes Tay Sachs disease in Ashkenazi Jews (Myerowitz, T., Proc. Natl. Aacd. Sci. USA, 85:3955 (1988)). A 5' splice junction mutation has been shown to be responsible for familial apolipoprotein A-II deficiency by blocking the splicing of intron 3 from the primary transcript (Deeb, S. S., et al., Am. J. Hum. Genet., 46:822 (1990)). A splice junction mutation in the steroid 21-hydroxylase gene is the most frequently detected mutation in patients with the salt-wasting and simple-virilizing forms of steroid 21-hydroxyase deficiency (Tajima, T., et al., Endoc. J., 45:291 (1998)). A type 2 Gaucher disease is caused by a rare splice junction mutation in the glucocerebrosidase gene (Reissner, K., et al., Mol. Genet. Metab., 63:281 (1998)). A splice-acceptor mutation in the KAL gene has led to Familiar Kallmann syndrome (O Neill, M. J., et. al., Hum. Mutat., 11:340 (1998)). A splice site mutation in the androgen receptor gene results in exon skipping and a non-functional truncated protein (Lim, J., et al., Mol. Cell. Endocrinol., 131:205 (1997)).

Mutations in promoters are also known to cause an increase, decrease, or abolition of gene expression. Therefore, a method to isolate a gene's control regions from a genomic DNA sample is very advantageous in genetic research. A primary objective of the invention is to overcome the deficiencies in the previous methods by providing appropriate primers and primer combinations that are effective and a method which isolates a given signal consensus sequence and its flanking sequence from most, if not all, of the locations where the signal sequence is present within a genome. A novel method that uses unique, full-length primers is presented herein. The novel method enables the specific amplification of the flanking regions to a given signal consensus sequence, such as the 3' splice junction, from multiple locations within a sample of genomic DNA. By this process, the invention creates a specific address for a particular gene control region from a particular gene in the genome such that this address can be used to amplify and sequence the same homologous region from different individuals for the purpose of discovering, for example, SNPs, or any other genetic lesion correlatable with a genetic disease (e.g., tri-nucleotide repeats, deletions or insertions of longer polymorphic sequences, denoted Simple Sequence Length Polymorphisms (SSLPs)).

The length of many signal sequences (e.g., promoters, poly A sites, 5' splice junctions, and 3' splice junctions) are shorter than optimal length for a standard primer conventionally used in PCR (see FIG. 2). In the invention, generally, randomized nucleotides (N) are added to a given consensus sequence of sub-optimal primer length to increase its length to a standard primer length (see FIG. 3). For example, the 8 nucleotide consensus sequence of the 5' splice junction forms a sub-optimal primer length (optimal primer lengths conventionally falling within the range of about 10 to 30 nucleotides), and is not useful as a conventional primer at standard stringent temperature of annealing in a standard PCR reaction. Either the temperature of annealing has to be lowered considerably, which will lead to significant non-specific binding, or the primer may not bind efficiently at the standard temperature of melting. This problem of sub-optimal length is even more apparent for promoter signals (5 to 6 nucleotides) and polyA signals (6 nucleotides). Increasing the length of the consensus sequence primer by adding a few randomized nucleotides imparts several advantages: 1) It increases the length of individual primers in the primer cocktail to a standard primer length. Each of the signal sequences in the genome represented by its consensus sequence and its flanking sequences, together comprising the standard primer length, will have a fully complementary primer species within the primer preparation. Therefore, each full-length primer species within the primer cocktail is a stand-alone primer for any given consensus sequence at a particular or unique location present in a template nucleic acid. Because the length of the primer is increased, a standard melting temperature can be employed in the PCR reaction. 2) It increases the specificity and binding affinity of individual primers contained in the primer preparation when each of them binds to a different binding site in the sample DNA. A mammalian genomic DNA sample contains perhaps one million different 5' splice junctions, each of which is of about 8 base pairs in length and which is identified by a consensus sequence. However, by adding randomized nucleotides to the consensus sequence, all the different possible sequences (of the length of the randomized nucleotides) adjacent to the signal consensus sequence, for example, at the 5' splice junction, are generated in the primer preparation, thereby providing an individual primer species with full sequence complementarity to each of the 5' splice junction sequences and a part of its flanking sequence within the DNA sample.

As noted above, a first primer with increased length, specificity and affinity, combined with the partly-fixed second primer, theoretically enables the specific PCR amplification of the sequences downstream from all occurrences of the targeted sequences present in a genomic DNA sample (see FIG. 4A). A library of these amplified sequences can be made by cloning them into an appropriate vector. Sequencing each of these clones, designing a reverse complementary primer downstream within the amplified target, and repeating the procedure to obtain the sequence upstream of the target results in the creation of a specific forward primer well upstream to the 3' splice junction of the exon. Thus, a unique forward and backward primer pair is created by this procedure for every unique exon in the sample. This primer pair is capable of specifically amplifying the unique exon and its flanking region from the genomic DNA.

Moreover, this primer pair can be applied across many different individuals for amplifying and sequencing the same specific exon from their respective genomic DNA, thereby enabling the discovery of any DNA sequence variation and thus any genetic lesion that correlates with a phenotypic condition.

The structure of the consensus sequence primer is different from that of the partly-fixed second primer. The consensus primer anchors a full-length primer species to a given targeted gene-control signal with a consensus sequence that has a sub-optimal length compared to a standard primer. The partly-fixed second primer enables a full-length primer to bind at an appropriate distance from the first primer-binding site (i.e., the site where the consensus primer binds). Thus, in the preferred embodiment, the specificity is imparted to the consensus sequence itself, and thereby its specific flanking sequence, in the design of the first primer only. The distance at which the second primer binds relative to the first primer in the template DNA is imparted in the design of the second primer, in a generally non-specific manner. The distance at which the second primer binds from the first primer is an average expected distance, and the fixed sequence at which it binds is arbitrary, and non-critical as far as the targeted sequence is concerned. In the preferred embodiment, the binding site for the second primer is not "targeted" as is the targeted consensus sequence.

That is not to say, however, that the second primer cannot be targeted in the same fashion as the first, consensus primer. Moreover, the second primer may be rc targeted to the same or a different consensus sequence as the first primer. As noted above, in the preferred embodiment, the first primer only is targeted to the specific sequences of interest and the second primer is non-specific, random and controls only distance (in nucleotides) between the binding site of the first primer and the second primer.

For example, the expected frequency of a fixed sequence of a 10-mer is roughly one in a million nucleotides ($4^{10}$). Thus, only 3000 occurrences are expected in the human genome of roughly $3\times10^9$ nucleotides. However, the splice junction sequences are present at about one million locations, considering the existence of 100,000 genes in the human genome and 5 to 10 exons per gene. The consensus sequence primers will bind at all of these locations, with a full-length primer at each location. There are one million primer binding sites that are specific to genes, and about 3000 that could occur non-specifically within the human genome. Therefore, the invention focuses on the one million true primer binding sites by using the specific full-length consensus sequence primers as the first primers, where only 3000 false splice sites may by bound by these primers. The ability of this process to anchor full-length first primers precisely to targeted sequences, therefore, is very advantageous in identifying and isolating a majority of the exons and flanking sequences from a genome.

In light of the disclosure contained herein, the invention is generally directed to a method of specifically amplifying desired regions of nucleic acid from a sample containing nucleic acid (see FIG. 4B). The method includes providing a plurality of first PCR primers, each first primer having a region of fixed nucleotide sequence complementary to a consensus sequence of interest and a region of randomized nucleotide sequence located 5' to, 3' to, anywhere within, or flanking the region of fixed nucleotide sequence. A plurality of second PCR primers is also provided, each second primer having a region of arbitrary, yet fixed nucleotide sequence and a region of randomized nucleotide sequence located 5' to, 3' to, anywhere within, or flanking the region of fixed nucleotide sequence. The nucleic acid present in the sample is then amplified via the PCR using the plurality of first PCR primers and the plurality of second PCR primers; whereby a subset of the plurality first primers binds to the consensus sequence of interest substantially wherever it occurs in the sample, and a subset of the plurality of second primers binds to the sample at locations removed from the first primers such that DNA regions flanked by the first primer and the second primer are specifically amplified.

The invention is further drawn to a method of specifically amplifying exons from a sample of genomic DNA (see FIGS. 5A and B). Here, the invention includes the steps of providing a plurality of first PCR primers, each first primer having a region of fixed nucleotide sequence corresponding to a consensus sequence of a 3' splice region and a region of randomized nucleotide sequence located 5' to, 3' to, anywhere within, or flanking the region of fixed nucleotide sequence. A plurality of second PCR primers is also provided, each second primer having a region of fixed nucleotide sequence reversely complementary to the consensus sequence of a 5' splice region and a region of randomized nucleotide sequence located 5' to, 3' to, anywhere within, or flanking the region of fixed nucleotide sequence. The genomic DNA is then amplified via the PCR using the plurality of first PCR primers and the plurality of second PCR primers; whereby a subset of the plurality first primers binds to the sequence reversely complementary to the 3' splice consensus sequence substantially wherever it occurs in the sample, and a subset of the plurality of second primers binds to the 5' splice consensus sequence substantially wherever it occurs in the sample, such that exons flanked by the first primer and the second primer are specifically amplified from the sample.

The invention is also drawn to a method of specifically amplifying the flanking regions of exons from a sample containing genomic DNA (see FIG. 6). The method can be used to isolate flanking regions on either end of an exon. The method includes a first step of amplifying the sequences downstream of the 5' splice signal sequence, which are present at multiple locations in a genome. This is accomplished by the method shown in FIG. 4B. The resulting PCR products are cloned into a library. The individuals clones are then sequenced to obtain the sequence downstream of the signal sequence. The obtained sequence is used to design a primer that will prime DNA synthesis in the opposite direction towards the signal and beyond. Using a partly-fixed second primer, the sequence towards the target exon is amplified from the genomic DNA and sequenced. The resulting sequence spans the 5' splice signal sequence, the exon including the 3' splice signal sequence, and beyond the exon into the previous intron.

A still further embodiment of the invention is drawn to a method of specifically amplifying regions flanking a consensus sequence in a sample of nucleic acid of totally or partially unknown sequence (see FIG. 7). Here, the invention includes the steps of providing a plurality of first PCR primers, each first primer having a region of fixed nucleotide sequence complementary to a consensus sequence of interest and a region of randomized nucleotide sequence located 5' to, 3' to, anywhere within, or flanking the region of fixed nucleotide sequence. A plurality of second PCR primers is also provided, each second primer having a region of arbitrary, yet fixed nucleotide sequence and a region of randomized nucleotide sequence located 5' to, 3' to, anywhere within, or flanking the region of fixed nucleotide sequence. The nucleic acid present in the sample is then amplified via the PCR using the plurality of first PCR primers and the plurality of second PCR primers; whereby a subset of the plurality first primers binds to the consensus sequence of interest substantially wherever it occurs in the sample, and a subset of the plurality of second primers binds to the sample at locations removed from the first primers, such that DNA regions flanked by the first primer and the second primer are specifically amplified. The plurality of the amplified sequences from the multiple regions within the sample are then cloned into a library via an appropriate vector. A portion of cloned DNA sequence downstream of the consensus region is sequenced. Using this sequence data, a third PCR primer with a unique nucleotide sequence which will prime PCR amplification in the 5' direction (i.e., upstream) from the sequenced portion of DNA, is provided. A plurality of fourth PCR primers is also provided, each fourth primer having a region of arbitrary, yet fixed nucleotide sequence and a region of randomized nucleotide sequence located 5' to, 3' to, anywhere within, or flanking the region of fixed nucleotide sequence. Lastly, the nucleic acid present in the sample is amplified via the PCR using the third PCR primer and the plurality of fourth PCR primers; whereby the third primer binds to the sequenced portion of nucleic acid from the first round of amplification, and a subset of the plurality of fourth primers binds to the sample at locations removed from the third primer such that DNA regions flanked by the third primer and the fourth primer are specifically amplified.

When cloned into an appropriate vector, the resulting fragments define a library of most fragments downstream of the multiple occurrences of the signal sequence. Any non-specific amplification between false signal sequences and the second primer, and between the juxtaposed second primers will also lead to fragments. These can be avoided during the clone selection analysis stage or by linking different restriction enzyme recognition sites on the ends of the two different primers for rare cutting enzymes that, statistically, will not cut within the amplified region.

Figure 5A:
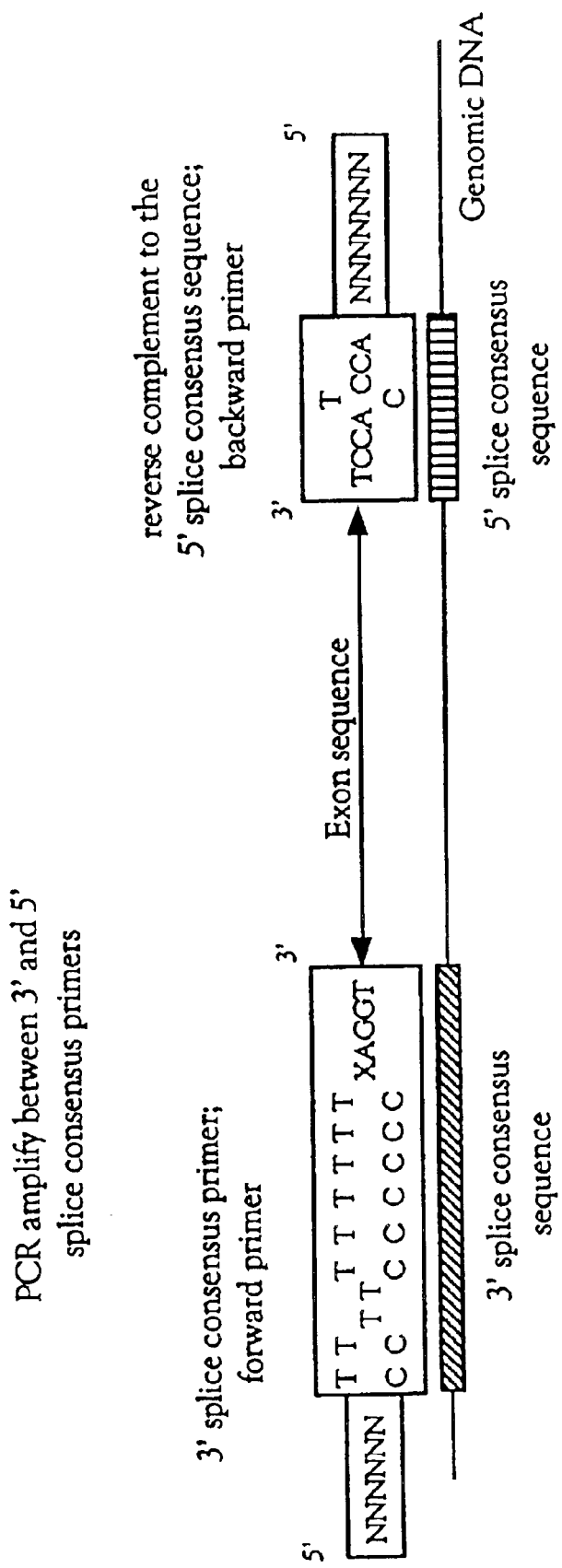
Figure 5B:
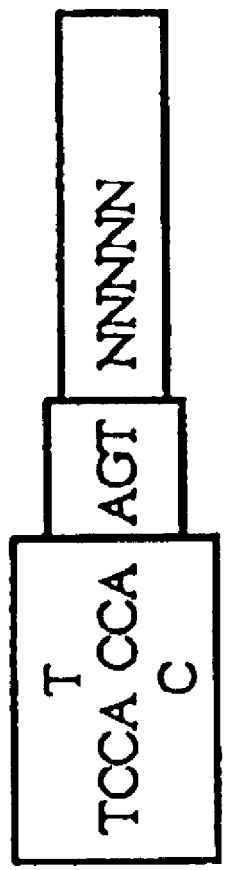

FIGS. 5A and 5B schematically represent isolating exon sequences from genomic DNA. Consensus sequence randomized primers are constructed from both 5' splice signal sequence and 3' splice signal sequence using the general method described in FIG. 3, in such a manner that the 3' splice signal is the first primer (forward primer) and the complementary sequence to the 5' splice signal is the second primer (backward primer), or vice-versa. PCR amplification between the two primers from a given genomic DNA will amplify the fragments between the two signal sequences present at multiple locations within the genome.

Figure 6:
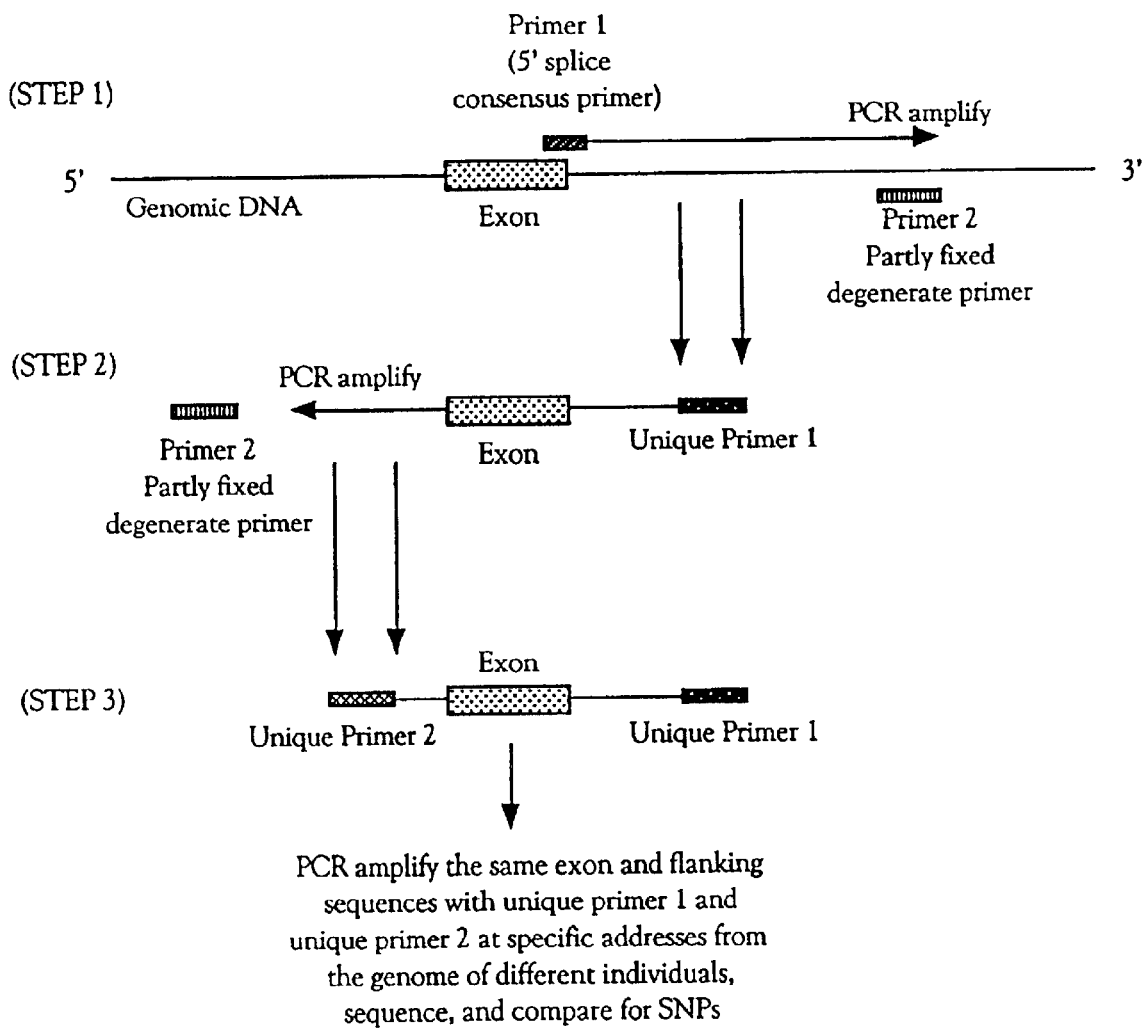

FIG. 6 illustrates isolating the flanking regions of exons from a genomic DNA. The objective is to isolate flanking regions on either or both ends of exons. In the first step, the sequences downstream of the 5' splice signal sequence, present at multiple locations in a genome, are amplified as described by the method shown in FIG. 4B, and cloned into a library. Individual clones representing each unique 5' splice signal present at a given unique location is sequenced to obtain the sequence downstream of the signal sequence. In the second step, a unique primer is designed from this sequence that will prime DNA synthesis in the opposite direction towards the signal and beyond. Using a partly-fixed second primer, the sequence towards the target exon is amplified from the genomic DNA and sequenced. The resulting sequence spans the 5' splice signal sequence, the exon including the 3' splice signal sequence and beyond the exon into the previous intron.

Figure 7:
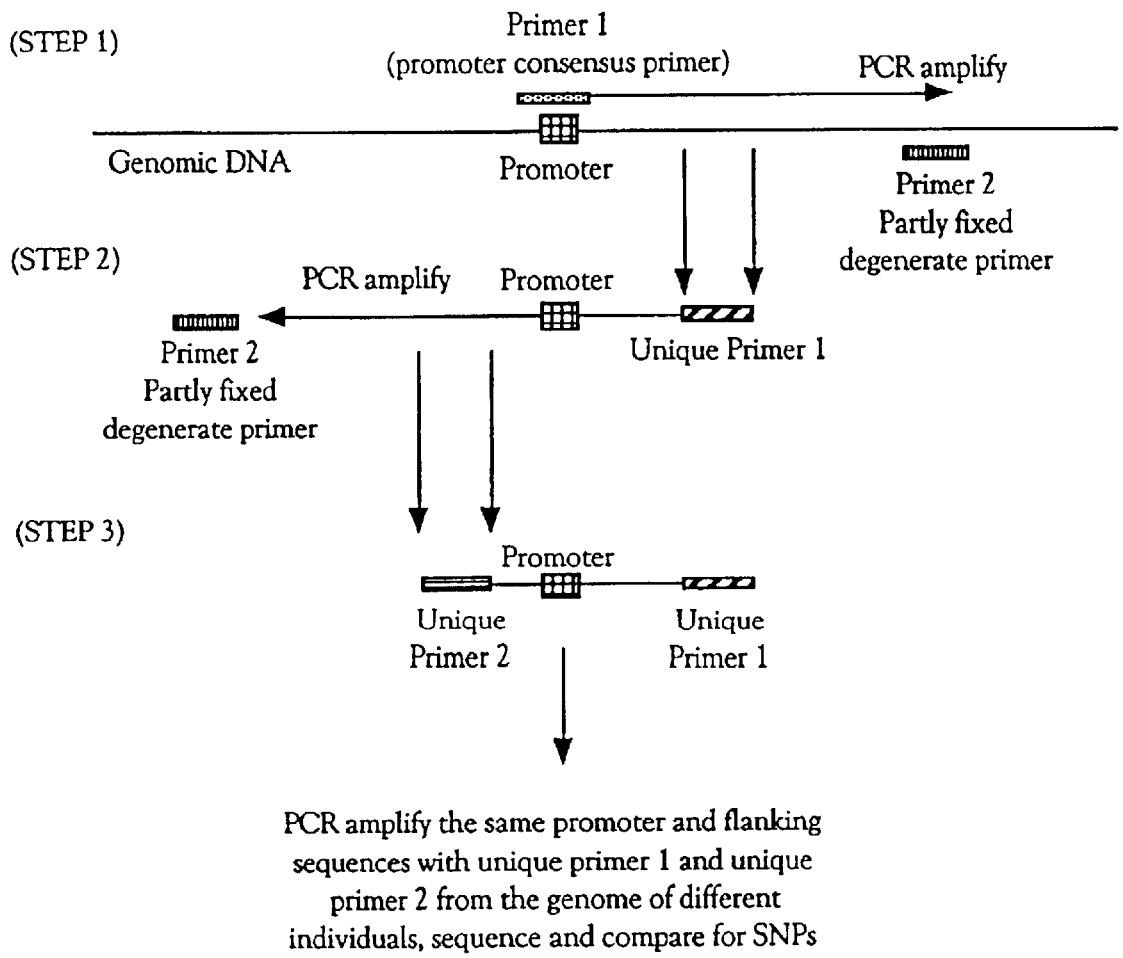

FIG. 7 illustrates isolation of the flanking regions (on both sides) of a given consensus randomized sequence from genomic DNA. The objective is to isolate the flanking regions on either ends of a given signal sequence, which is present at multiple locations within a given genome. In the first step, the sequences downstream of the signal sequence present at multiple locations in a genome are amplified as described by the randomized consensus PCR in FIG. 4B, and cloned into a library. Individual clones representing each unique signal present at a given location within the genome is sequenced to obtain the sequence downstream of the signal sequence. In the second step, a unique primer is designed from the sequence from a given clone that will prime DNA synthesis in the opposite direction towards the signal and beyond. Amplifying from sample DNA using this unique primer and a partly-fixed second primer, and then sequencing the amplified fragment, sequences a portion of DNA that spans the consensus sequence on both sides to a considerable extent. The length of the sequence can be controlled by using a longer fixed base sequence in the partly-fixed second primer.

DETAILED DESCRIPTION

Definitions:

To provide a clear and consistent understanding of the specification, the following definitions are used herein. 5' Splice and 3' Splice Regions (or Junctions)—The regions of DNA defining the upstream and downstream boundaries of an intron. The sequences of 5' splice regions are conserved, as are the sequences of 3' splice regions.

Alu Repeats—A family of conserved, short interspersed elements of genomic DNA which contain the recognition sequence for the AluI restriction enzyme (AGCT). In mammals, Alu repeats occur about 1 million times throughout the genome.

Consensus Sequence—Sub-sets or families of relatively short, repetitive DNA sequences which appear throughout eukaryotic (and prokaryotic) organisms. Non-limiting examples of consensus sequences include promoters, Alu repeats, splice regions, etc. Variations may occur within the repetitive seqeunces. A consensus of the most frequent nucleotides appearing at each position of the repeat is derived, which is then defined as the consensus sequence for the particular type of repeat. For purposes of the present invention, a consensus sequence is any sequence of DNA which is repeated many times throughout a genome and which can be used as a PCR priming site.

Exons—The part of the DNA of a gene that encodes the information for the actual amino acid sequence of the encoded protein.

Homeobox—A highly conserved sequence of DNA that occurs in the coding region of development-controlling regulatory genes and codes for a protein domain that is similar in structure to certain DNA-binding proteins and is thought to be involved in the control of gene expression during morphogenesis and development.

Introns—A region of DNA in a eukaryotic gene, usually on the order of hundreds to tens of thousands of base pairs long, that is not expressed in the encoded protein molecule or mature RNA. Introns divide the DNA of a single eukaryotic gene into a number of non-contiguous stretches.

Operationally-Linked—When referring to joined DNA sequences, "operationally-linked" denotes that the sequences are in the same reading frame and upstream regulatory sequences will perform as such in relation to downstream structural sequences. DNA sequences which are operationally-linked are not necessarily physically linked directly to one another but may be separated by intervening nucleotides which do not interfere with the operational relationship of the linked sequences.

Poly A Sites—A sequence of DNA that directs the addition of poly A's to a messenger RNA molecule.

Polymerase Chain Reaction (PCR)— A technique in which cycles of denaturation, annealing with a primer pair, and extension with DNA polymerase are used to generate a large number of copies of a desired polynucleotide sequence. See U.S. Pat. Nos. 4,683,195 and 4,683,202 for a description of the reaction. The PCR is widely used in manipulation of nucleic acids.

Promoter—The DNA sequence site where RNA polymerase binds to the beginning of an operon. Once bound, the RNA polymerase travels along the DNA in the 5' to 3' direction and assembles the corresponding RNA sequences. While the promoter functions as the start signal for RNA synthesis, the promoter itself is not transcribed.

Figure 1:
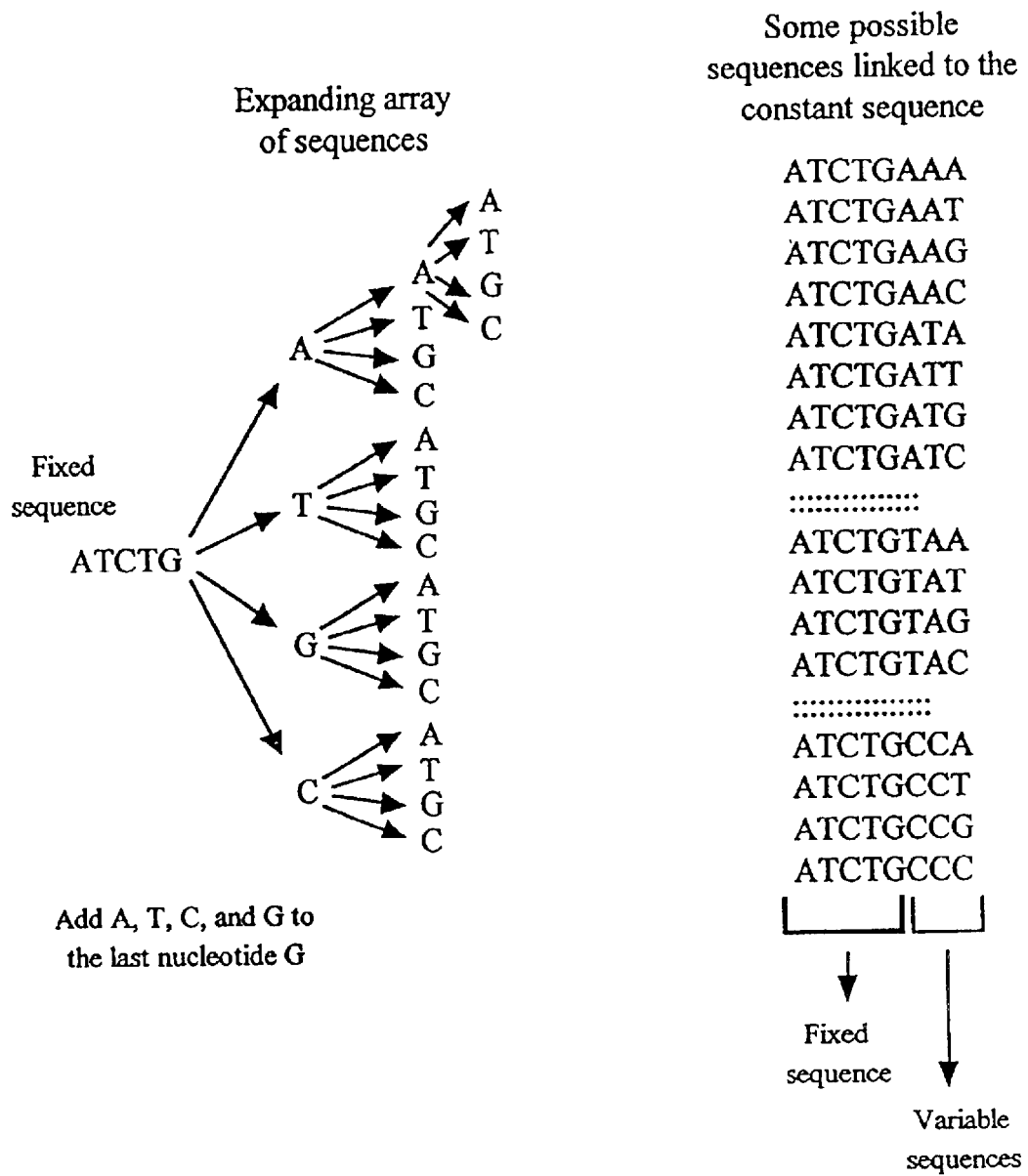
FIG. 1 is a schematic representation of the array of primers created with the invention.

Randomized Sequence—A fixed sequence, to which all of the 4 nucleotides (Ns) are linked in a parallel manner, and subsequently repeating this step in a sequential manner. Parallel addition of Ns, (i.e., A, G, C, T) are linked in a parallel manner. Ns are added at the endnucleotide of a fixed sequence. For example, if the end-nucleotide is G, all four nucleotides are linked to the G, producing GA, GG, GC, and GT. A subsequent addition of N to this primer preparation again will link all the four nucleotides to the 3' end of all the four species of primers, resulting in 16 possible sequences, namely, GAA, GAG, GAC, GAT, GGA, GGG, GGC, GGT, GCA, GCG, GCC, GCT, GTA, GTG, GTC, and GTT. Subsequent repetition of this step will link all the four nucleotides (i.e., Ns) to all the possible sequences that resulted in the previous step (i.e., to the n-1st randomized nucleotide(s)). This process will generate an exponentially expanding array of random sequences as the number of added Ns increases (see FIG. 1). All of the possible sequences of length N ($_4$N different sequences) will be linked to the fixed sequence, and will be present in the fully randomized oligonucleotide prepared in this manner.

Signal Sequence—A stretch of DNA or RNA sequence within a gene or a genome that functions as a signal for a molecular activity. For instance, a promoter sequence signals the attachment of an RNA polymerase enzyme to it and the further transcription of the gene. A splice junction sequence signals to the spliceosomal machinery the splicing together of the exons and editing out of the introns in the primary RNA sequence. Poly-A addition site, Alu sequence, homeobox sequence, and microsatellite sequence are other examples of signal sequences.

Template Nucleic Acid or Nucleic Acid Sample—DNA or RNA to be analyzed using the subject method. The source for the nucleic acid to be analyzed is irrelevant. Isolating DNA and RNA from virtually any source is extremely well known. The invention functions with equal success using nucleic acid from any source, including eukaryotic, procaryotic, animal, plant (both monocot and dicot), fungi, algae, and virus nucleic acids, DNA and RNA included, without limitation.

Genetic Engineering:

Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described extensively in Sambrook, J., E. F. Fritsch, and T. Maniatis, (1989), "Molecular Cloning: A Laboratory Manual," Cold Spring Harbor Laboratory Press: New York, N.Y.

General Approach:

The invention is a method for isolating the flanking regions to any type of consensus sequence, or to whole exons from multiple sites in a nucelic acid template or sample, preferably a DNA sample, including a genomic DNA sample, a sub-genomic DNA sample, cloned genomic DNA, individual chromosomes, and a sub-chromosomal DNA sample. The invention is described for use with genomic DNA for illustrative purposes only, not to limit the invention. The invention, for example, enables the specific isolation of most if not all splice junctions (both 5' and 3') or the exon sequences with their flanking regions, from genomic DNA.

Figure 2:
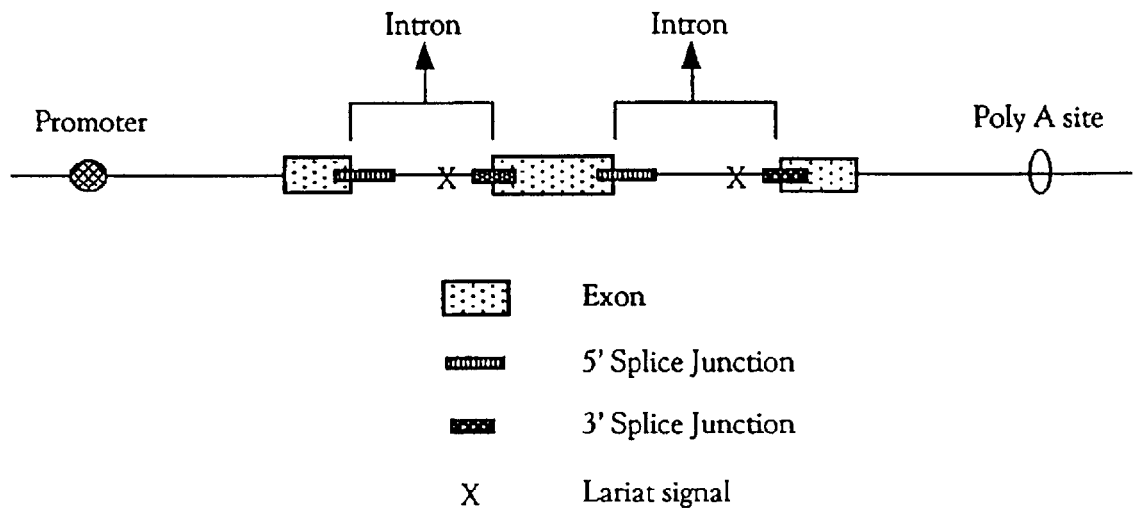
FIG. 2 is a schematic representation of various transcriptional and translational signal consensus sequences found in a typical mammalian genome.

In one embodiment, the invention uses the consensus sequence of the 3' splice junction or the 5' splice junction or both for designing a first and/or a second primer which includes, along with the consensus sequence of interest, a stretch of randomized nucleotide sequences (see FIG. 2). The first primer may include a few randomized nucleotides in addition to the consensus sequence such that each of the targeted regions in the genes in a genome will have a specifically matching primer sequence in the primer preparation. A sub-set of the first primers will therefore not only bind to the consensus sequence but also to a few more nucleotides that flank the targeted sequence (on either one side or both sides, depending upon where the random nucleotides N are situated in the first primer relative to the consensus sequence portion of the primer).

Figure 3:
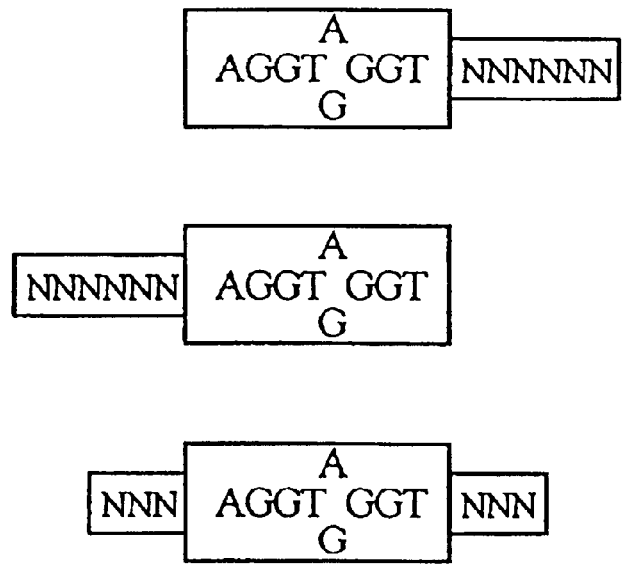
FIG. 3 shows the design of a first, consensus primer from a given consensus sequence with sub-optimal primer length. The consensus sequence is designed to be included in the full-length primer sequence. A sufficient number of randomized nucleotides (N) are added to the consensus sequence in such a manner that the total length of the primer is at least about 10 to about 30 nucleotides. Examples of primer design from a promoter consensus sequence site and a 5' splice junction consensus sequence are shown.
Figure 3:
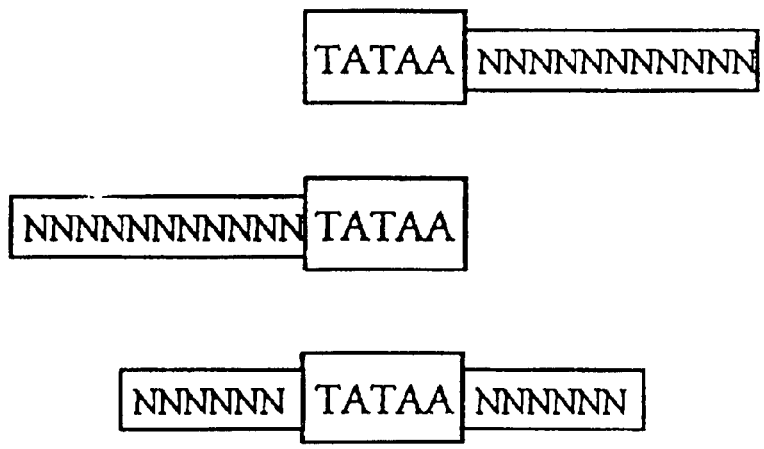

Referring specifically to FIG. 2, the 5' splice junction consensus sequence is generally 8 bp long and the 3' splice junction consensus sequence is generally about nucleotides long (i.e., equivalent to the total number of individual bases). Thus, a first primer can be designed to include the 5' splice junction consensus sequence of about 8 nucleotides, and, in addition, a few randomized nucleotides (N) are added to make the primer sufficiently long to function well in the PCR. "N" in the figures represents any of the four nucleotide bases, namely, A, T, C, and G. As shown in FIG. 3, the randomized nucleotides N can be added to either the 3' or the 5' end of the consensus sequence or to both ends of the consensus sequence.

Figure 4A:
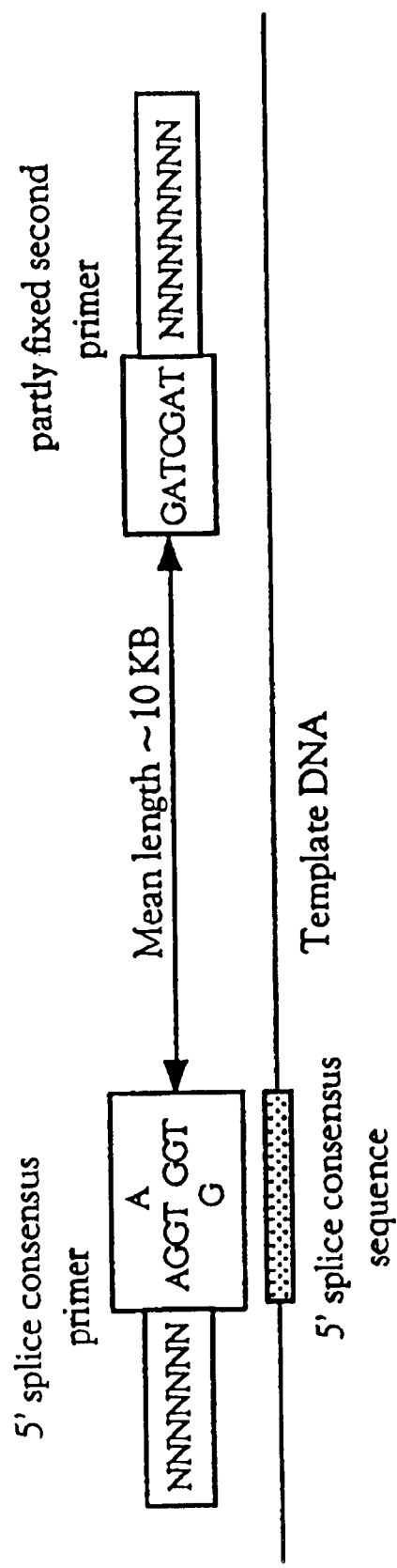
FIG. 4A schematically illustrates the general method of the present invention, referred to herein as randomized consensus PCR. A sufficient number of randomized nucleotides (N) are added to a consensus sequence to make its length equivalent to a standard primer for PCR. This sequence is used as the first primer. The second primer includes a partly-fixed portion, in which the fixed-sequence length determines the mean length at which the second primer will bind on a template with respect to the first primer (general formula: mean length=$4^n$, where n is the number of fixed nucleotides). A standard PCR amplification between the first and the second primer will amplify the DNA fragment between them.
Figure 4B:
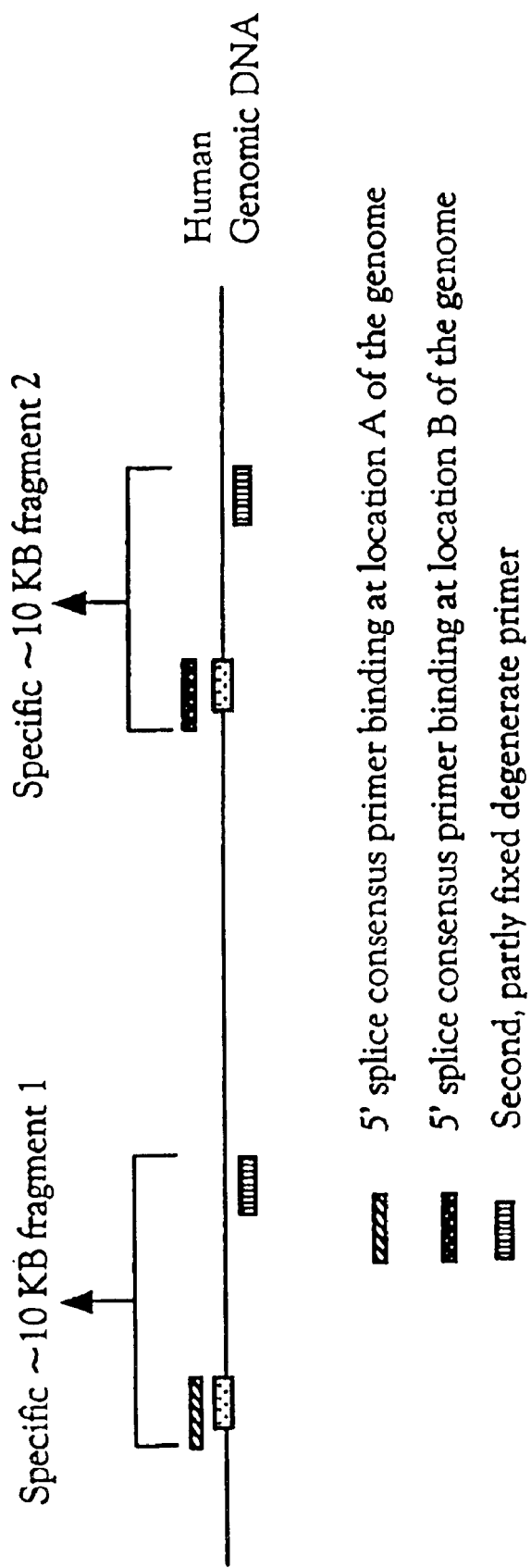
FIG. 4B illustrates how the process shown in FIG. 4A occurs simultaneously at all occurrences of the consensus sequence because the consensus sequence is repetitively present at many locations within the genome. Consequently, the fragments between most of these consensus sequences and the closest occurring second primer is amplified. At each consensus location, a fully complementary first primer species will bind. A fully complementary second primer species will bind at a second primer binding site determined by the fixed sequence in the second primer downstream of the first primer.

Using the 5' splice junction as an example, and referring specifically to FIG. 4A, if the total length of the first primer is desired to be 15 nucleotides, then the primer preparation will contain all the species of primer sequences that will bind all of the 5' splice junctions that are defined by the consensus sequence, and the 7 additional nucleotides (N) 5' to the consensus sequence. In other words, in the preferred embodiment, all possible sequence combinations of the 7 randomized nucleotides N are represented in the plurality of first primers. See FIG. 4A, "Randomized 5' splice consensus primer, forward primer." There are roughly 64,000 possible sequences with 8 additional random nucleotides, and these possible sequences are a subset of all of the one million or so 5' splice junctions estimated to be present in the human genome. Because there are about one million 5' splice junctions in the human genome, statistics indicate that each of the primer species will specifically bind to about 16 different splice junctions in the genome. However, if 10 additional randomized nucleotides (N) are added to the consensus nucleotides (8 nucleotides) to yield a first primer 18 nucleotides long, the primer preparation will contain literally all of the possible one million or so different 10-mer sequences adjacent to the 5' consensus sequence in the human genome. In this situation, each primer subspecies in the primer preparation will bind to a unique 5' splice junction region within the genome.

The use of a partly-fixed second primer then enables the binding of a full-length second primer at an appropriate distance (for example, 1 kb for a 5-base fixed primer) from each of the locations wherever the first primer (i.e., the 5' splice consensus primer) binds. The use of primers designed to anneal to fixed sequences that occur more frequently in a sample DNA is advantageous for the same purpose. PCR amplification of the fragments between each of the first primer-second primer pair yields specific amplification of the 3' flanking regions of exons, i.e. the region between the 5' splice junction and the downstream second primer.

The advantage of this process is that a PCR amplification by a full-length primer pair is enabled at each of the consensus sequence locations, although the sequence downstream of a consensus sequence is completely unknown in the genomic DNA. The 10 additional randomized nucleotides (N) downstream, upstream, or on either side of each splice site consensus sequence, can be different and unique at each of the splice sites within the genome. Even so, a particular primer species within the primer cocktail will bind with full complementarity with all 18 nucleotides at the particular consensus site. Therefore, at each specific splice junction in each specific gene, a particular species of primer sequence present in the primer preparation will bind specifically and with standard complementarity.

The randomized nucleotides are added to the splice junction consensus sequence of the primer to increase the primer sequence length from, for example 8 to 18 nucleotides, or to any manageable length of a standard PCR primer, and to increase the specificity and affinity of binding to the targeted consensus site within the DNA sample.

The randomized Ns are added to the consensus sequence portion of the first primer in a sequential manner to the previous base position in, preferably, a fully representational fashion, thereby yielding a plurality of first primers in which all possible sequences with the length of added Ns are generated in the primer preparation. Consequently, if 8 additional N's are added, preferably 4$^8$ different sequences, which is all of the possible sequences available for an 8-base random sequence portion, will be present within the plurality of primers. This makes it possible for a full-length primer to be present in the preparation for every splice site location (or any other targeted location) present in the DNA sample.

For instance, when only 6 random nucleotides are added to the 10-base consensus sequence of the 3' splice consensus sequence to yield a 16-mer, the 4096 different possible sequences of the random portion are the subset of all of the approximately one million possible 3' splice junction sequences expected to be present in the human genome. Using this primer, all of these million splice junction sequences will be primed by the primer. Again, the important underlying advantage of adding random nucleotides to the first primer is to increase the length of the primer so that it functions well in standard PCR. The increased length of the first primer (which also contains the targeted consensus sequence) increases the specificity and binding affinity of each of the primer species at its specific binding site.

Another advantage of adding randomized sequences (Ns) to a consensus sequence is to make available specific primer species that bind with a longer, unique sequence, at each site of the consensus sequence in a sample DNA. This randomized primer and the specific PCR method afford the power of uniqueness to many primer species within the primer preparation, making unique sequences surrounding the consensus sequence within a sample DNA specifically accessible for complementary binding. Manipulations other than PCR can also be based on this unique complementary binding.

The $T_M$ of 10-base sequence with 50% GC content is 30° C., whereas that of a 16-base sequence is 48° C. (computed using 2° C. for each A and T, and 4° C. for each G and C; i.e., $\Delta T_m = 4°(G+C)+2° (A+T)$). Non-specific binding can be reduced at higher temperatures of annealing.

The reverse complementary sequence for the consensus sequence of a 5' splice junction could also be used to design a primer, such that the DNA priming and synthesis will begin at the 5' splice junction and proceed in the opposite, upstream direction, toward the target exon bounded by the particular splice junction.

Similarly, a primer with the 3' splice junction can be designed to include 6 fixed nucleotides (corresponding to the consensus site), 8 partially fixed nucleotides (TC/TC/TC/TC), and the rest randomized nucleotides. The total number of fixed nucleotides in this case is 10 nucleotides. This primer will amplify the DNA sequence downstream of it, i.e., toward the exon downstream from it. The reverse complement of this sequence can also be used to make a primer that will prime DNA synthesis on the opposite strand in the opposite direction.

Another embodiment of the invention is to use the approach disclosed above to prime shorter consensus sequences such as promoter regions or poly A sites. The promoter consensus sequence is generally about 5 nucleotides. If 11 random Ns are added to the 5-base consensus sequence, each primer species will be present at a very low concentration within the primer preparation.

To increase the concentration of the primers, each of the four nucleotides can be used in a separate primer preparation to reduce the required number of random nucleotides in the primer by one. That is, in separate preparations add A, T, C, or G to the 5' base consensus sequence, to which are then added 10 randomized Ns instead of 11. Likewise, each of 64 possible triplets are added to the 5' base consensus sequence to yield an 8-base fixed primer sequence in separate reactions, to which only 8 random Ns are added (see FIG. 5B). The PCR reaction is then conducted in 64 separate tubes.

The resulting PCR amplification products are then combined before the library is built. Alternatively, 64 separate libraries could be prepared, each representing a specific 8-base fixed sequence. This process is easily implemented using conventional equipment universally found in a moderately equipped molecular biology laboratory.

Specific Amplification of Exons:

Referring now to FIGS. 5A and 5B, PCR amplification can be carried out between a first primer which is a partly-fixed 3' splice consensus primer and a second primer that is the reverse complement to a partly-fixed 5' splice consensus primer. In this instance, specific exon sequences that are included between the first primer and the second primer will be specifically amplified. Each amplified sequence will begin at the 3' splice junction and end at 5' splice junction of a particular exon of a gene. This PCR amplification approach will amplify a majority of the exon sequences that are bounded by the consensus sequences used in the design of the 3' and the 5' splice consensus primers.

The important advantage of this method is that each unique exon is amplified by its own unique primer pair, a primer pair that is fully complementary not only to its specific 3' and 5' splice junction sequences, but also to an additional, longer sequence adjacent to them.

Amplification of the Exons and Their Flanking Regions:

Referring now to FIG. 6, the objective in this embodiment is not only to amplify the exons precisely delimited by their splice junctions, but also exons and a considerable portion of the DNA flanking them on either (or both) side(s). In order to achieve this goal, three steps are undertaken. First, a PCR amplification can be carried out between the 5' splice consensus primer as the first primer, and a partly-fixed degenerate primer as the second primer. (The second, degenerate primer is the subject matter of allowed patent application Ser. No. 081406,545, incorporated herein by reference). The object is to amplify a fragment of about 1000 nucleotides downstream from the 5' splice site (i.e., from the 3' end of the exon) into the following intron.

In this case, the second primer-binding site and its distance from the first primer binding site within the intron are determined by the number of nucleotides in the fixed-sequence portion of the second primer and the fixed-sequence portion of the second primer. Thus the second primer will bind at an approximate, predetermined average length from the first primer, e.g., 1024 nucleotides from the first primer when the second primer includes 5 fixed nucleotides.

The amplified product is the fragment extending from the partly-fixed 5' splice consensus primer (the first primer) and the partly-fixed second primer, which will bind downstream of the 5' splice consensus primer within the downstream intron.

For obtaining long DNA fragments containing the splice Junctions or exons, long range PCR can be used in the method described in Senapathy, allowed patent application Ser. No. 08/406,545, now U.S. Pat. No. 5,994,098, issued Nov. 30, 1999, by including longer fixed sequences in the degenerate primers.

Any non-specificity can be avoided by fine-tuning the reaction conditions such as by adjusting the annealing temperature and the reaction temperature during amplification, and/or adjusting the length and G/C content of the primers. These adjustments are routinely done in the standard PCR amplification protocol in short, although the partly-fixed primers have a random sequence component, a sub-population of the primer molecules will have the exact sequence that would bind with the exact target sequence. The proportion of the molecules with exact sequence that would bind with the exact target sequence will vary depending on the number of random characters in the partly-fixed primers. For example, a primer 11 nucleotides long with 6 characters fixed and 5 characters random, one in about 1000 primer molecules will have the exact sequence complementary to the target sequence on the template.

By increasing the concentration of the primers appropriately, a comfortable level of PCR amplification required for sequencing can be achieved. When primer concentration is increased. It requires an increase in the concentration of magnesium, which is required for the function of the polymerase enzyme. The excess primers (and "primer-dimers" formed due to excess of primers) can be removed after amplification reaction by a gel-purification step.

Any non-specific binding by any population of the primers to non-target sequences can be avoided by adjusting (increasing) the temperature of re-annealing appropriately during DNA amplification. It is well known that the change of even one nucleotide due to point-mutation in some cancer genes can be detected by DNA-hybridization. Hybridization is routinely used for diagnosing particular cancer genes (e.g., John Lyons, "Analysis of ras gene point mutations by PCR and oligonucleotide hybridization," in PCR Protocols: A guide to methods and applications, edited by Michael A. Innis et al., (1990), Academic Press, New York). This is done by adjusting the "re-annealing" or "melting-temperature", and fine-tuning the reaction conditions. Thus the binding of non-specific sequences even with just one nucleotide difference compared to the target binding-site in the template sequence can be avoided.

The minimum length of primer for highly specific amplification between primers on a template DNA is usually considered to be about 15 nucleotides. However, in the present invention, this length can be reduced by increasing the G/C content of the primers to 12–14 nucleotides.

During the amplification, numerous fragments will be amplified, each from a particular splice junction. All of these fragments can then be cloned from the genomic DNA of one particular human individual (or other species) as a library. Each of the clones can be sequenced by any means now known or developed in the future. The advantage of this approach is that the downstream flanking regions of most splice junction sequences from most genes can be targeted for amplification, and each individual region can be sequenced.

Using the information from the first step, in the second step, a unique primer can be designed from the newly-sequenced region, downstream from a 5' splice site within the intron from a particular exon (i.e. from a particular clone), which will be specific to a given gene (see FIG. 6). The unique primer is designed from the newly-sequenced region on the opposite strand in the direction toward the target exon, which will be the first, 5' to 3' primer for this PCR reaction. A manageable length of sequence in the direction of the target exon, e.g., about 1,000 to 10,000 nucleotides can be obtained using a second primer of partially-fixed and partially random sequence as described above. Generally, approximately 1000 nucleotides will include the entire exon upstream, as well as both the 5' and 3' splice junction sequences, and a reasonable amount of intronic sequence data flanking both sides of the exon. This sequence is expected to include any functional SNPs within the introns. The reason for this expectation is that most exons are of lengths shorter than 600 nucleotides, and only rarely are exons longer than 600 nucleotides (Senapathy, P., Proc. Natl. Acad. Sci. USA, 83:2133–37 (1986); ibid., 85:1129–33 (1988); ibid, Science, 268:1366–67 (1995); Senapathy, P., et al., Methods in Enzymol., 183:252–78 (1990)).

In the third step, another unique primer from the subsequently sequenced region upstream of the target exon is designed such that this unique primer, and the unique primer that was designed downstream of the exon in the second step above, will amplify the exon and its flanking region on either side. The unique primer pair is specific to the particular exon such that a PCR amplification using this primer pair on the genomic DNA of another individual will specifically amplify the same exon. This allows the genomes of individuals to be compared for mutations in or surrounding a given exon.

The total number of genes in the human genome is estimated to be about 100,000. Each gene may have, on average, 5–10 exons. Thus, a rough estimate of all exons in a mammalian genome is about 500,000. Using the present invention, most if not all exons and their flanking regions can be sequenced. This method can be used to analyze the genomic DNA of one individual. This individual can then serve as a reference. Unique primers upstream and downstream of each exon can be designed from the reference sequences. These unique primers then serve as the specific address for a given exon in the entire genome.

The invention thus enables the design of two unique primers for each exon within a genomic DNA, thereby allowing the amplification of the exon and its flanking regions on either (or both) side(s), even though the exon sequence was unknown a priori. The unique primer pair for a given exon of a particular gene thus forms the address for that exon and its flanking sequences on either (or both) side(s) across different individuals of the same species or even different species. Working with a population of individuals of the same species, for example, *Homo sapiens*, the sequence of this exon can be obtained from many different individuals so that they can be compared for the express purpose of discovering polymorphisms, mutations, SNPs, etc, literally any divergence in the sequence of the given exon and its flanking regions between individuals. By sequencing different groups of individuals, any sequence differences associated with these individual groups can be associated with a particular phenotype or disease state.

Specialized computer programs can be used to compare nucleotide sequences to determine the presence of SNPs in a given exon/flanking sequence. Also, additional clustering computational methods can assess if any functional SNPs are associated with given traits of particular group of individuals. Each of the exons can be sequenced from a large number of individuals, and grouped and compared by any number of significant sub-populations, such as phenotypically normal individuals from different racial or ethnic groups, phenotypically abnormal individuals, or allopatrically isolated groups, such as some Icelandic groups or religious groups which are known to be highly inbred and wherein a significant number of linkage studies have already been completed.

Flanking sequences of a particular exon can also be isolated by other techniques. For example, an exon sequence can be obtained from an exon clone isolated as described under "Specific Amplification of Exons" above. This exon sequence lacks its flanking sequences. A unique primer can be designed near the 5' end or the 3' end of a particular exon from the sequence of the clone. PCR amplification using this primer and a partly fixed second primer amplifies the specific sequence downstream (or upstream) of the unique primer, which can then be sequenced. Doing this on both ends of the exon results in the flanking sequences of the exon.

Isolating other Gene-Control Signal Sequences Such as Promoters:

This approach can be applied not only to splice junction signals but also to other transcriptional and/or translational control signals that are shorter than standard primer length.

Referring now to FIG. 7, consensus sequences exist for promoters and poly A sites. In each of these cases, a primer can be prepared to include the consensus sequence as the fixed portion of the first primer, while adding a number of randomized nucleotides to increase the length to a manageable standard PCR primer length. A partly-fixed second primer is then used to PCR amplify the sequence between the first primer and the second primer. The advantage of this approach is that the first primer with randomized nucleotides in addition to the consensus sequence nucleotides, enables each of the many different species of primers to bind to a different but specific location within the genome, wherein the consensus sequence and a unique surrounding sequence make up the total binding site. Furthermore, the partly-fixed second primer in this approach enables it to bind to a specific sequence downstream of the first primer, from wherever the first primer binds in the template DNA. Thus, a unique sequence downstream of each of the promoter sequences can be PCR amplified and sequenced.

This approach can also be used to obtain sequences around active sites of proteins, by defining a consensus sequence around the active site amino acids. Variable nucleotides and random nucleotides can be added at required locations of the consensus sequence, and additional randomized nucleotides added to increase the length to a standard primer length.

The approach can be applied to any organism and any type of source DNA, although its full benefits are realized when using genomic DNA of eukaryotes. The consensus sequences for various control regions are often very similar in different organisms, thus allowing the present invention to be used to evaluate phylogenetic relationships between different species. Also, there are distinct repeated sequences in different organisms, such as the human, mouse, and *Drosophila*. These specific repeated sequences can be used with the current invention to obtain any SNPs around them in particular organisms.

To maximize the amplification of consensus sequences with flanking sequences whose G+C content is low, and, therefore, whose $T_m$ is low, a randomized consensus primer or a second, degenerate primer can be designed wherein the random nucleotides at each position will have a lower than 50% G+C content. This allows a higher proportion of A- or T-containing sequences adjacent to the consensus sequence to be binding sites. The $T_m$ of the primer designed will be lower than expected for an average G+C content sequence, and can be computed as a function of the proportion of the G+C content. Different proportions of G+C, from 0 to 100%, can be used to cover a wide range of sequences with lower G+C content and higher A+T content. With low G+C content, sequences containing mostly A or T are made so that a resulting randomized consensus sequence primer will have mostly A- or T- containing random portions adjacent to the consensus sequence. This process enables the PCR reaction of higher G+C content primers separately, and a higher A+T content separately.

A PCR reaction using higher G+C content primers at a lower than optimum $T_m$ may cause nonspecific amplification of DNA fragments. The process of adjusting G+C content during the preparation of the degenerate primer avoids the problem of not being able to amplify sequences bounded by higher A+T content. Also, one can use different proportions of A or T at a given nucleotide location within the primer, or G or C, or other combinations thereof to enable different sets of nucleotides in the possible sequences.

Non-standard nucleotides (minor bases or universal bases), such as inosine or 5-nitro-indole can also be used at some positions within a degenerate primer to enable any nucleotide from a template sequence position to bind to it.

Arbitrary Sequence Primers as Unique Addresses in a Genome:

The current invention can also be used to obtain sequences from completely unknown regions of a genome. An arbitrary sequence primer of length n, where $4^n$ is approximately the length of the genome, for example, $3 \times 10^9$ for the human genome, is prepared. Here n is approximately 15 nucleotides. Adding 5 randomized nucleotides, N, to the 15 nucleotides yields a 20-mer primer. Statistically, because a given 15-mer sequence has only one exact match in a genome of this size, a 20-mer which includes the same fixed 15-mer sequence plus 5 added random Ns will also only match at that unique location (with the addition of the five flanking nucleotides). The rest of the primer species will remain in solution because there is no complementary site within the genome for binding.

The added Ns in this case serve to increase the length, specificity and affinity of the primer to its specific binding site in the genome, over and above what the 15-mer affords. PCR using this first primer and partly-fixed second primer as discussed above will amplify one specific fragment from the first primer location.

Universal bases, such as inosine or 5-nitro-indole, can be used as tails to these primers for increasing the affinity of the primer to its binding site.

Alternatively, a 10-mer primer sequence of interest can be increased in length by the addition of 6 randomized Ns. The total number of primer species in this 207 preparation is 4096. PCR with this primer cocktail and a second degenerate primer will theoretically amplify all of the 4096 locations appearing in the genome which are bounded by each first primer species and the second primer binding site downstream of the first primer.

The same process holds true for any consensus sequence present in a genome, such as the different Alu sequences in a genome or the different homeobox sequences. The Alu (approximately 250 nucleotides) or homeobox (approximately 180 nucleotides) sequences are relatively long as compared to promoter regions and splice regions. Consequently, full-length primers can be designed from them, with Ns added for any variable nucleotides. A second, degenerate primer is used along with the Alu or homeobox primer. This enables the discovery of SNPs or SSLPs present in the different Alu sequence sites and their flanking regions in a genome or the different homeobox and flanking sequences in a genome.

A considerable number of developmental traits may be associated with sequences in and around homeobox sequences.

In all of the methods described herein, the consensus sequence for a particular signal may exhibit mutations within the sequence, or variations from the norm not covered by the consensus sequence. Therefore, the randomized primer created in the invention described herein can comprise random nucleotide(s) at such mutational positions(s) also. This enables the complementary binding of these primers with the particular consensus sequence locations within a sample DNA exhibiting such mutations. These mutations within a consensus sequence can be analyzed by using consensus primers with Ns at different positions within the consensus sequence. These "mutant" primers enable the binding of the primers to "mutated" sites, or genuine sites that are variant from the consensus sequence. Furthermore, the resulting amplified fragments will reveal such mutations by their subsequent sequencing analysis.

The subject invention is not limited to the exact manipulations and protocols described hereinabove, but encompasses all such equivalent forms thereof as come within the scope of the following claims.

What is claimed is:

1. A method of amplifying desired regions of nucleic acid from a nucleic acid template comprising:
   (a) providing a plurality of first PCR primers, each first prune having an overall length of from about 10 nucleotides to about 30 nucleotides and further having a region of fixed nucleotide sequence identical or complementary to a consensus sequence of interest and a region of randomized nucleotide sequence located 5' to, 3' to, or fuming the region of fixed nucleotide sequence;
   (b) providing a plurality of second PCR primers, each second primer having an overall length of from about 10 nucleotides to about 30 nucleotides and further having a region of arbitrary, yet fixed nucleotide sequence and a region of randomized nucleotide sequence located 5' to, 3' to, or flanking the region of fixed nucleotide sequence; and then
   (c) amplifying the nucleic acid template via the PCR using the plurality of first PCR primers and the plurality of second PCR primers under conditions wherein a subset of the plurality first primers binds to the consensus sequence of interest substantially wherever it occurs in the template, and a subset of the plurality of second primers binds to the template at locations removed from the first primers such that nucleic acid regions flanked by the first primer and the second primer are specifically amplified.

2. The method of claim 1, wherein the template is genomic DNA.

3. The method of claim 1, wherein the template is eukaryotic genomic DNA.

4. The method of claim 1, wherein template is human genomic DNA.

5. The method of claim 1, wherein the template is prokaryotic DNA.

6. The method of claim 1, wherein the template is DNA selected from the group consisting of cloned genomic DNA, a subgenomic region of DNA, a chromosome, and a sub-chromosomal region.

7. The method of claim 1, wherein the template is RNA.

8. The method of claim 1, wherein in step (a) is provided a plurality of first PCR primers, each first primer having a region of fixed nucleotide sequence complementary to a consensus sequence selected from the group consisting of a promoter sequence, a 3' splice sequence, a 5' splice sequence, an Ala repeat, a tandem repeat, poly-A site, a lariat signal, a microsatellite sequence, and a homeobox sequence.

9. The method of claim 1, wherein in stop (a) is provided a plurality of first primers having a G+C content selected from the group consisting of over 50%, under 50%, and about 50%, and in step (b) is provided a plurality of second primers having a G+C content selected from the group consisting of over 50%, under 50%, and about 50%.

10. The method of claim 1, further comprising step (d): incorporating the amplified fragments of step (c) into a library.

11. A method of amplifying exons from a nucleic acid template comprising:
   (a) providing a plural of first PCR primers, each first primer having an overall length of from about 10 nucleotides to about 30 nucleotides and further having a region of fixed nucleotide sequence identical or complementary to a consensus sequence of a 3' splice region and a region of randomized nucleotide sequence located 5' to, 3' to, or flanking the region of fixed nucleotide sequence;

(b) providing a plurality of second PCR primers, each second primer having an overall length of from about 10 nucleotides to about 30 nucleotides and further having a moon of fixed nucleotide sequence reversely complementary to a consensus sequence of a 5' splice region and a region of randomized nucleotide sequence located 5' to, 3' to, or flag the region of fixed nucleotide sequence; and then (c) amplifying the nucleic acid template via the PCR using the polity of first PCR primers and the plurality of second PCR primers under conditions wherein a subset of the plurality first primers binds to a sequence reversely complementary to the 3' splice consensus sequence substantially wherever it occurs in the template, and a subset of the plurality of second primers binds to the 5' splice consensus sequence substantially wherever it occurs in the template, such that exons flanked by the first primer and the second primer are specially amplified.

12. The method of claim 11, wherein in step (a) is provided a plurality of first primers having a G+C content selected from the group consisting of cover 50%, under 50%, and at 50%, and in step (b) is provided a plurality of second primers having a G+C content selected from the group consisting of cover 50%, under 50%, and at 50%.

13. The method of claim 11, further comprising step (d): incorporating the, amplified fragments of step (c) into a library.

14. The method of claim 11, wherein a genomic DNA template is amplified.

15. The method of claim 11, wherein a human genomic DNA template is specifically amplified.

16. The method of claim 11, wherein a DNA template selected from the group consisting of cloned genomic DNA, a subgenomic region of DNA, a chromosome, and a sub-chromosomal region is amplified.

17. A method of amplifying regions flanking a consensus sequence in a nucleic acid template of totally or partially unknown sequence comprising:

(a) providing a plurality of first PCR primers, each first primer having an overall length of from about 10 nucleotides to about 30 nucleotides and further having a region of fixed nucleotide sequence identical or complementary to a consensus sequence of interest and a region of randomized nucleotide sequence located 5' to, 3' to, or flanking the region of fixed nucleotide sequence;

(b) providing a plurality of second PCR primers, each second primer having an overall length of from about 10 nucleotides to about 30 nucleotides and further having a region of arbitrary, yet fixed nucleotide sequence and a region of randomized nucleotide sequence located 5' to, 3' to, or flanking the region of fixed nucleotide sequence, then (c) amplifying the nucleic acid template via the PCR using the plurality of first PCR primers and the plurality of second PCR primers under conditions wherein a subset of the plurality fist primers binds to the consensus sequence of interest substantially wherever it occurs in the template, and a subset of the plurality of second primers hinds to the template at locations removed from the fist priers such that nucleic acid regions flanked by the first primer and the second primmer are specifically amplified; then (d) incorporating the amplified nucleic acid of step (c) into a library;

(e) sequencing a portion of amplified nucleic acid from a particular clone from the library of step (d) and providing a third PCR primer of unique sequence and having an overall length of at least about 10 nucleotides which will prime PCR amplification from the sequenced portion of DNA;

(f) providing a plurality of fourth PCR primers, each fourth primer having an overall length of at least about 10 nucleotides and further having a region of arbitrary, yet fixed nucleotide sequence and a region of randomized nucleotide sequence located 5' to, 3' to, ox flanking the region of fixed nucleotide sequence; and then (g) amplifying the nucleic acid present in the template via the PCR using the third PCR primer and the plurality of fourth PCR primers under conditions wherein the third primer binds to the sequenced portion of nucleic acid from step (e), and a subset of the plurality of fourth primers binds to the template at locations removed from the third primers such that nucleic acid regions flanked by the third primer and the fourth primer are specifically amplified.

18. The method of claim 17, wherein the template is genomic DNA.

19. The method of claim 17, wherein the template is eukaryotic genomic DNA.

20. The method of claim 17, wherein the template is human genomic DNA.

21. The method of claim 17, wherein the template is prokaryotic DNA.

22. The method of claim 17, wherein the template is DNA selected from the group consisting of cloned genomic DNA, a subgenomic region of DNA, a chromosome, and a sub-chromosomal region.

23. The method of claim 17, wherein the template is RNA.

24. The method of claim 17, wherein in step (a) is provided a plurality of first PCR primers, each fist primer having a region of fixed nucleotide sequence identical or complementary to a consensus sequence selected from the group consisting of a promoter sequence, a 3' splice sequence, a 5' splice sequence, an Alu repeat, a tandem repeat, poly-A site, a lariat signal, a microsatellite, and a homeobox sequence.

25. The method of claim 17, wherein in step (a) is provided a plurality of first primers having a G+C content selected from the group consisting of cover 50%, under 50%, and at 50%, and in step (b) is provided a plurality of second primers having a GC content selected from the group consisting of cover 50%, under 50%, and at 50%.

26. The method of claim 17, further comprising step (h): incorporating the specifically amplified fragments of step (g) into a library.

* * * * *